United States Patent [19]
Trauner et al.

[11] Patent Number: 5,942,534
[45] Date of Patent: Aug. 24, 1999

[54] PHOTODYNAMIC THERAPY FOR THE TREATMENT OF OSTEOARTHRITIS

[75] Inventors: Kenneth Trauner, Sacramento, Calif.; Tayyaba Hasan, Arlington, Mass.

[73] Assignee: The General Hospital Corporation, Boston, Mass.

[21] Appl. No.: 08/948,623

[22] Filed: Oct. 10, 1997

Related U.S. Application Data

[60] Provisional application No. 60/028,198, Oct. 10, 1996.
[51] Int. Cl.$^6$ ................................................. A01N 43/38
[52] U.S. Cl. ..................... 514/410; 514/561; 514/429; 514/825
[58] Field of Search ................... 514/561, 825, 514/410, 429

[56] References Cited

U.S. PATENT DOCUMENTS

| | | | |
|---|---|---|---|
| 5,028,594 | 7/1991 | Carson | 514/23 |
| 5,079,262 | 1/1992 | Kennedy et al. | 514/561 |
| 5,211,938 | 5/1993 | Kennedy et al. | 424/7.1 |
| 5,234,940 | 8/1993 | Kennedy et al. | 514/410 |
| 5,368,841 | 11/1994 | Trauner et al. | 424/9 |
| 5,422,093 | 6/1995 | Kennedy et al. | 424/9.61 |

OTHER PUBLICATIONS

Allison et al., "The Plasma Distribution of Benzoporphyrin Derivative And The Effects of Plasma Lipoproteins On Its Biodistribution," Photochem. Photobiol. 52: 501–507 (1990).

Allison et al., "The Effects of Plasma Lipoproteins On In Vitro Tumor Cell Killing And In Vivo Tumor Photosensitization With Benzoprophyrin Derivative," Photochem. Photobiol. 54: 709–715 (1991).

Auler et al., "Untersuchungen über die Rolle der Porphyrine bei geschwulstkranken Menschen und Tierch," Z. Krebforsch 53: 65–68 (1942).

Beems et al., "Photosensitization Properties of Bacteriochlorophyllin α And Bacteriochlorin α, Two Derivatives of Bacteriochlorophyll α," Photochem. Photobiol. 46: 639–643 (1987).

Bottiroli et al., "Equilibrium Among Hematoporphyrin-–Derivative Components: Influence of The Interaction With Cellular Structures," Photochem. Photobiol. 47: 209–214 (1988).

Brault, "Physical Chemistry of Porphyrins And Their Interactions With Membranes: The Importance of pH," J. Photochem. Photobiol, B: Biology 6: 79–86 (1990).

Dougherty et al., "Photodynamic Therapy For The Treatment of Cancer: Current Status And Advances," Photodynamic Therapy of Neoplastic Disease, Kessel Ed., chapter 1: 1–19 (1989).

Figge et al., "Cancer Detection And Therapy. Affinity of Neoplastic, Embryonic, And Traumatized Tissues For Porphyrins And Metalloporphyrins," Proc. Soc. Exp. Biol. Med. 68: 640–641 (1948).

Gomer, "Preclinical Examination of First and Second Generation Photosensitizers Used In Photodynamic Therapy" Photochem. Photobiol. 54: 1093–1107 (1991).

Gross, "Spectroscopic Determination of Hematoporphyrin-–Membrane Partition Parameters," Photobiological Techniques, Series A: Life Sciences 216: 117–126 Plenum Press, New York (1991).

Gurinovich et al., Photodynamic Activity of Chlorin $e_6$ and Cholorin $e_6$ Ethylenediamide In Vitro and In Vivo J. Photochem. Photobiol. B: Biol. 13: 51–57 (1992).

Henderson et al., "Studies On The Mechanism of Tumor Destruction By Photoradiation Therapy," Porphyrin Localization and Treatment of Tumors, Liss, New York pp. 601–612 (1984).

Jori et al., "Strategies For Tumor Targeting By Photodynamic Sensitizers," Photodynamic Therapy of Neoplastic Disease, 2: 117–130 (1989).

Jori et al., "Photothermal Sensitizers: Possible Use In Tumor Therapy," J. Photochem. Photobiol. B: Biology 6: 93–101 (1990).

Kessel, "Sites of Photosensitization By Derivatives of Hematoporphyrin," Photochem. Photobiol 44: 489–493 (1986).

Kessel, "Interactions Between Porphyrins And Mitochondrial Benzodiazepine Receptors," Cancer Letters 39: 193–198 (1988).

Kessel et al., "Photosensitization With Derivatives of Chlorophyll," Photochem. Photobiol 49: 157–160 (1989).

Kessel, "Determinants of Photosensitization By Purpurins," Photochem. Photobiol. 50: 169–174 (1989).

Kreimer–Birnbaum, "Modified Porphyrins, Chlorins, Phthalocyanines, and Purpurins: Second–Generation Photosensitizers for Photodynamic Therapy," Sem. in Hematol. 26: 157–173 (1989).

Lipson et al., "The Use of A Derivative of Hematoporphyrin In Tumor Detection," JNCI 26: 1–10 (1961).

Maziere et al., "Cellular Uptake And Photosensitizing Properties of Anticancer Porphyrins In Cell Membranes And Low And High Density Lipoproteins," J. Photochem. Photobiol., B: Biology 6: 61–68 (1990).

Maziere et al., "New Trends In Photobiology (Invited Review) The Role Of The Low Density Lipoprotein Receptor Pathway In The Delivery of Lopophilic Photosensitizers In The Photodynamic Therapy of Tumours," J. Photochem. Photobiol., B: Biology 8: 351–360 (1991).

Morgan et al., "New Sensitizers for Photodynamic Therapy: Controlled Synthesis of Purpurins And Their Effect On Normal Tissue," J. Med. Chem. 32: 904–908 (1989).

Morgan et al., "Metallopurpurins And Light: Effect On Transplantable Rat Bladder Tumors And Murine Skin," Photochem. Photobiol. 51: 589–592 (1990).

(List continued on next page.)

Primary Examiner—Theodore J. Criares
Attorney, Agent, or Firm—Fish & Richardson P.C.

[57] ABSTRACT

A method of treating a patient who has osteoarthritic disease by administering a therapeutic composition containing a photoactivatable compound, or a precursor thereof, and administering light of a photoactivating wavelength that activates the compound.

15 Claims, 5 Drawing Sheets

OTHER PUBLICATIONS

Poon et al., "Laser–Induced Fluorescence: Experimental Intraoperative Delineation of Tumor Resection Margins" J. Neurosurg 76: 679–686 (1992).

Pottier, "In Vitro And In Vivo Fluorescence Monitoring of Photosensitizers," J. Photochem. Photobiol, B: Biology 6: 103–109 (1990).

Ricchelli et al., "Factors Influencing The Distribution Pattern of Porphyrins In Cell Membranes," J. Photochem. Photobiol., B: Biology 6: 69–77 (1990).

Reddi et al., "Liposome– or LDL– Administered Zn (II)—Phthalocyanine As A Photodynamic Agent For Tumours. I. Pharmacokinetic Properties And Phototherapeutic Efficiency," Br. J. Cancer 61: 407–411 (1990).

Richter et al., "Photosensitizing Potency of Structural Analogues of Benzoporphyrin Derivative (BPD) In A Mouse Tumour Model," Br. J. Cancer 63: 87–93 (1991).

Salet, et al., "Photosensitization of Isolated Mitochondria By Hematoporphyrin Derivative (PhotoFrin®): Effects On Bioenergetics," Photochem. Photobiol. 53: 391–393 (1991).

Weishaupt, et al., "Identification of Singlet Oxygen As The Cytotoxic Agent In Photo–Inactivation of A Murine Tumor," Cancer Research 36: 2326–2329 (1976).

PHOTODYNAMIC THERAPY FOR THE TREATMENT OF OSTEOARTHRITIS

This application claims priority from U.S. Provisional application Ser. No. 60/028,198, filed on Oct. 10, 1996, which is incorporated herein by reference in its entirety.

This invention was made in part with government support under grant number DEFG02-91-ER61228 awarded by the Department of Energy. The United States government has certain rights in the invention.

BACKGROUND OF THE INVENTION

The invention relates to photodynamic therapy.

Photodynamic therapy (PDT) was first developed as an experimental treatment for cancer. The treatment was based on the observation that cancer cells could retain photoactivatable compounds and could be selectively killed when these compounds subsequently interacted with absorbed light (see e.g., Bottiroli et al., Photochem. Photobiol. 47:209–214, 1988; Salet et al., Photochem. Photobiol. 53:391–393, 1991; Gross, In Photobiological Techniques, Valenzeno et al. Eds., Plenum Press, New York, 1991; and Jori et al., In Photodynamic Therapy of Neoplastic Disease, Kessel Ed., CRC Press, Boca Raton, Fla., 1989). A photodynamic compound that is widely used is marketed as Photofrin®. Photofrin®/HPD (hematoporphyrin derivative) was the first FDA approved photosensitizing agent available for PDT trials. Photofrin® has subsequently been tested extensively for the destruction of multiple tumors in numerous medical disciplines (Dougherty et al., In Photodynamic Therapy of Neoplastic Disease, Kessel Ed., supra).

The mechanism of action for hematoporphyrin derivatives such as Photofrin® in the treatment of neoplastic disease is well delineated. Large molecular aggregates of the porphyrins accumulate around tumor neovasculature. This accumulation is caused by poor lymphatic drainage from the neoplastic tissues. Once sequestered in the tissue, the molecular aggregates dissociate, and the hydrophobic components of the porphyrin cause it to partition into cell membranes, primarily into the cellular and mitochondrial membranes.

Initiation of photodynamic activity is caused by excitation of the photodynamic compound by light that falls within its absorption band. The wavelength specificity depends on the molecular structure of the photodynamic compound; a greater degree of conjugation within a molecule leads to greater absorbance at longer wavelengths. Activation of photodynamic compounds occurs with subablative light fluences. Toxicity is achieved by $O_2$ radical toxicity. The singlet $O_2$ reacts with, for example, double bonds to produce reactive species, for example, organoperoxides. These, in turn, initiate free radical chain reactions which degrade and disorganize membranes, uncouple oxidative phosphorylation, and lead to cellular disruption (Jori et al., supra; Weishaupt et al., Cancer Res 36:2326–2329, 1976). Nucleic acids and proteins are also damaged by photooxidation (Henderson et al., In Porphyrin Localization and Treatment of Tumors, Doiron et al. Eds., Liss, N.Y., 1984).

Studies demonstrating destruction of synovium without significant side effects indicate that photochemical synovectomy is an effective treatment for rheumatoid arthritis (U.S. Pat. No. 5,368,841).

SUMMARY OF THE INVENTION

The invention features a method of treating a patient who has an osteoarthritic joint by administering a photoactivatable compound, or a precursor thereof, and administering light of a wave-length that activates the compound. The method of the invention may be used to treat a human patient or another mammal, such as a dog, cat, rabbit, horse, cow, sheep or non-human primate.

Another embodiment of the invention is the use of a photoactivatable compound, or a precursor thereof, for the manufacture of a medicament for treating a patient who has an osteoarthritic joint. This treatment involves administering the medicament containing the photoactivatable compound, or a precursor thereof, and administering light of a wavelength that activates the compound.

Photoactivatable compounds can be administered to a patient according to established guidelines, so that the concentration of the compound in the target tissue (i.e., in the joint) will be greater than the concentration of the compound in the surrounding tissue. The ratio of the compound in the affected tissue to the compound in the surrounding tissue is preferably 2:1 or greater. Furthermore, the compound may be administered so that an adequate level of the compound will be maintained in the target tissue. In general, this objective, i.e., an adequate level of a differentially localized compound, can be achieved using standard techniques known to skilled pharmacologists in which the clearance time course for the compound is considered.

Compounds may be administered either systemically or locally to the area of the joint. Systemically or locally administered compounds that are useful in the invention include those that are preferentially taken up by the target tissue or those that are retained substantially longer by the target tissues than by the surrounding tissues of a patient. Furthermore, photoactivatable compounds may be administered alone, or in mixtures containing two or more such compounds. If compounds are combined, light of an effective wavelength for each compound in the mixture must be used to photoactivate the compounds.

Generally, the photoactivatable compound used must have a sufficiently low toxicity to permit administration to a patient with a medically acceptable level of safety. Various photoactivatable compounds are known and can be used in the practice of the invention. These compounds typically have chemical structures that include multiple conjugated rings that allow for light absorption and photoactivation. They differ in the properties of light absorption and fluorescence, biodistribution, temporal uptake, and clearance. Classes of photoactivatable compounds include hematoporphyrins (Kessel, Cancer Lett. 39:193–198, 1988), uroporphyrins, phthalocyanines (Kreimer-Birnbaum, Sem. in Hematol. 26:157–173, 1989), purpurins (Morgan et al., Photochem. Photobiol. 51:589–592, 1990; Kessel, Photochem. Photobiol. 50:169–174, 1989), acridine dyes, bacteriochlorophylls (Beems et al., Photochem. Photobiol. 46:639–643, 1987; Kessel et al., Photochem. Photobiol. 49:157–160, 1989), and bacteriochlorins (Gurinovich et al., J. Photochem. Photobiol. B-Biol. 13:51–57, 1992). Specific photoactivatable compounds which may be used to treat osteoarthritis are summarized, in part, in Table 1. Any photoactivating compound which displays no systemic toxicity and which is useful for photodynamic therapy of neoplasias may generally be useful in the methods of the invention. Preferably, Photofrin® (which is semi-purified hematoporphyrin derivative), benzoporphyrin derivatives, or aminolevulinic acid is administered in accordance with the invention.

TABLE 1

Compounds for Photodynamic Therapy of Osteoarthritis

1. Photofrin®
2. Synthetic diporphyrins and dichlorins

3. Hydroporphyrins such as chlorins and bacteriochlorins of the tetra(hydroxyphenyl) porphyrin series
4. phthalocyanines (PC)
   with or without metal substituents,
   e.g., chloroaluminum phthalocyanine (CASP)
   with or without varying substituents
5. O-substituted tetraphenyl porphyrins
   (picket fence porphyrins)
6. 3,1-meso tetrakis (o-propionamido phenyl) porphyrin
7. Verdins
8. Purpurins
   tin and zinc derivatives of octaethylpurpurin (NT2)
   etiopurpurin (ET2)
9. Chlorins
   chlorin e6
   mono-l-aspartyl derivative of chlorin e6
   di-l-aspartyl derivative of chlorin e6
10. Benzoporphyrin derivatives (BPD)
    benzoporphyrin monoacid derivatives
    tetracyanoethylene adducts of benzoporphyrin
    dimethyl acetylenedicarboxylate adducts of benzoporphyrin
    Diels-Adler adducts
    monoacid ring "a" derivative of benzoporphyrin
11. sulfonated aluminum PC
    sulfonated AlPc
    disulfonated ($AlPcS_2$)
    tetrasulfonated derivative
    sulfonated aluminum naphthalocyanines
12. naphthalocyanines
    with or without metal substituents
    with or without varying substituents
13. anthracenediones
14. anthrapyrazoles
15. aminoanthraquinone
16. phenoxazine dyes
17. phenothiazine derivatives
18. chalcogenapyrylium dyes
    cationic selena and tellurapyrylium derivatives
19. ring-substituted cationic PC
20. pheophorbide derivative
21. hematoporphyrin (HP)
22. other naturally occurring porphyrins
23. 5-aminolevulinic acid and other endogenous metabolic precursors
24. benzonaphthoporphyrazines
25. cationic imminium salts
26. tetracyclines In addition to free photactivatable compounds, photoactivatable compounds may be delivered in various formulations, including liposomal, peptide/polymer-bound, or detergent-containing formulations.

An alternative to administration of the photoactivatable compound itself, is administration of a precursor of that compound. This approach is illustrated by the use of 5-aminolevulinic acid, which causes endogenous production of the photoactivatable compound protoporphyrin IX (Morgan et al., J. Med. Chem. 32:904–908, 1989).

Light of the appropriate wavelength for a given compound may be administered by a variety of methods known to one skilled in the art. These methods may involve laser, nonlaser, or broad band light and may result in either extracorporeal or intraarticular generation of the light of the appropriate wavelengths. Light used in the invention may be administered using any device which generates the appropriate wave form including, but not limited to, fiber optic instruments, arthroscopic instruments, or instruments which provide transillumination, as is known to one of ordinary skill in the art.

The therapeutic method described herein can provide effective treatment for osteoarthritic joints and the inflammation that may accompany any mechanical injury of a joint. As described herein, photoactivatable chemicals are administered, and the local joint region is then exposed to light via optical fibers threaded through small gauge hypodermic needles. Alternatively, the light source may be provided extracorporeally by transillumination. Thus, photodynamic therapy offers an effective, novel, and minimally invasive treatment which may benefit a large number of patients; 60–80% of the population develop some degree of osteoarthritis during their lifetime.

The invention also features an in vitro method for screening for a photoactivatable compound useful in PDT of osteoarthritis. The method involves contacting chondrocytes with the test photoactivatable compound, administering light of an appropriate wave length and determining whether this treatment has decreased the number of viable chondrocytes. Compounds that decrease the number of viable chondrocytes after treatment with light can be useful for PDT of osteoarthritis.

The term "osteoarthritic disease" as used herein is meant to encompass primary osteoarthritis, which may be of unknown etiology, and secondary osteoarthritis, which may occur as the result of a degenerative arthrosis. A patient that has osteoarthritis and, accordingly, an "osteoarthritic joint," may or may not have apparent focal damage, such as lesions, on the articular surfaces of an affected joint. It is expected that most patients availing themselves of the method of treatment described herein will be symptomatic, but the treatment may be also be applied as a prophylactic measure.

As used herein, "precursor" means a compound that is metabolically converted to a photoactivatable compound after administration to a patient.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. Unless otherwise indicated, these materials and methods are illustrative only and are not intended to be limiting. All publications, patent applications, patents and other references mentioned herein are illustratiive only and not intended to be limiting.

Other features and advantages of the invention, e.g., treatment of human osteoarthritis, will be apparent from the following description, from the drawings and from the claims.

DETAILED DESCRIPTION

Figure 1A:
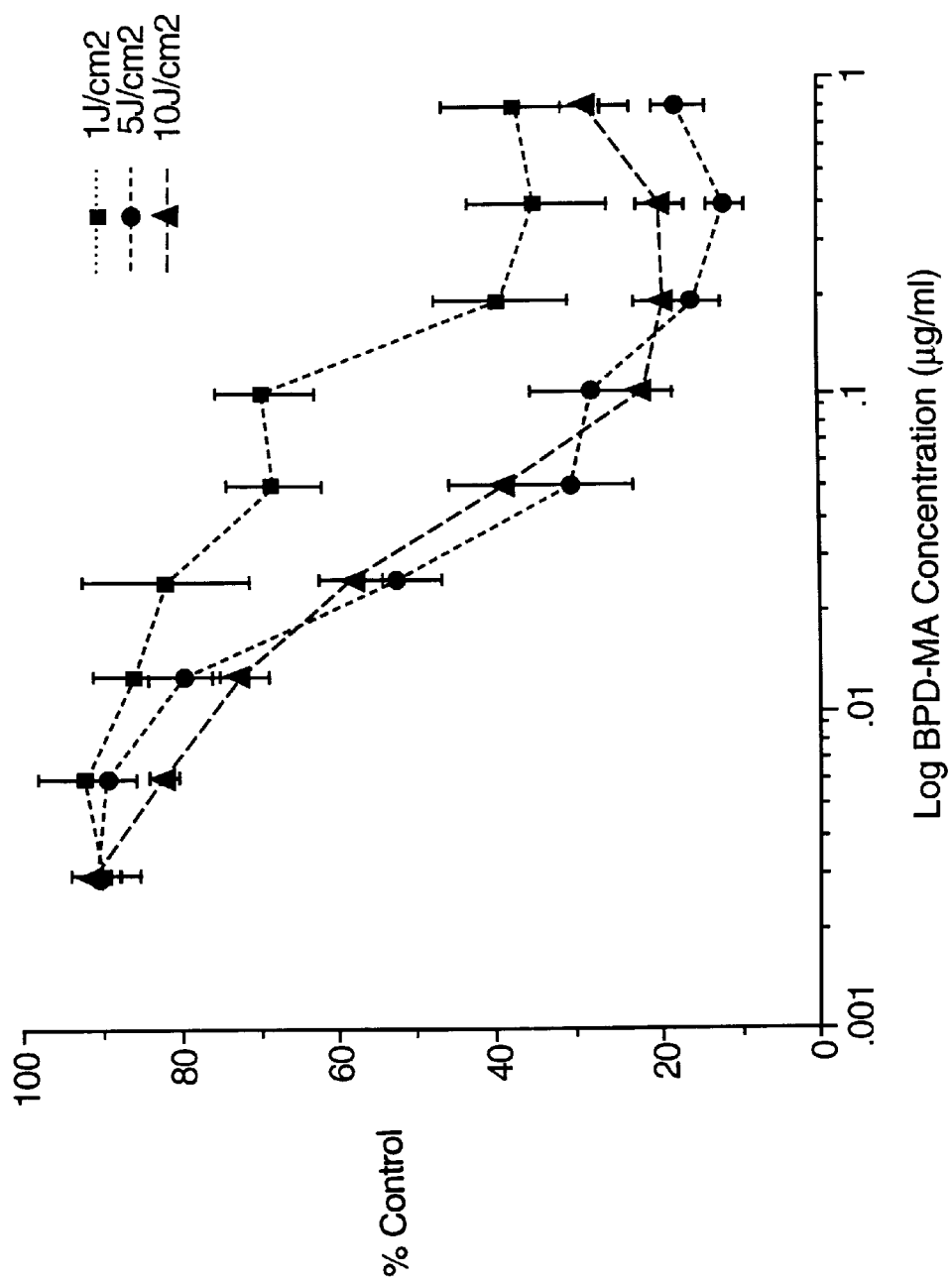
FIGS. 1A–1D are line graphs depicting the effect of PDT on chondrocyte viability using BPD-MA (FIG. 1A), Ce6 (FIG. 1B), PF (FIG. 1C) or CASP (FIG. 1D) as the photosensitizer.
Figure 1B:
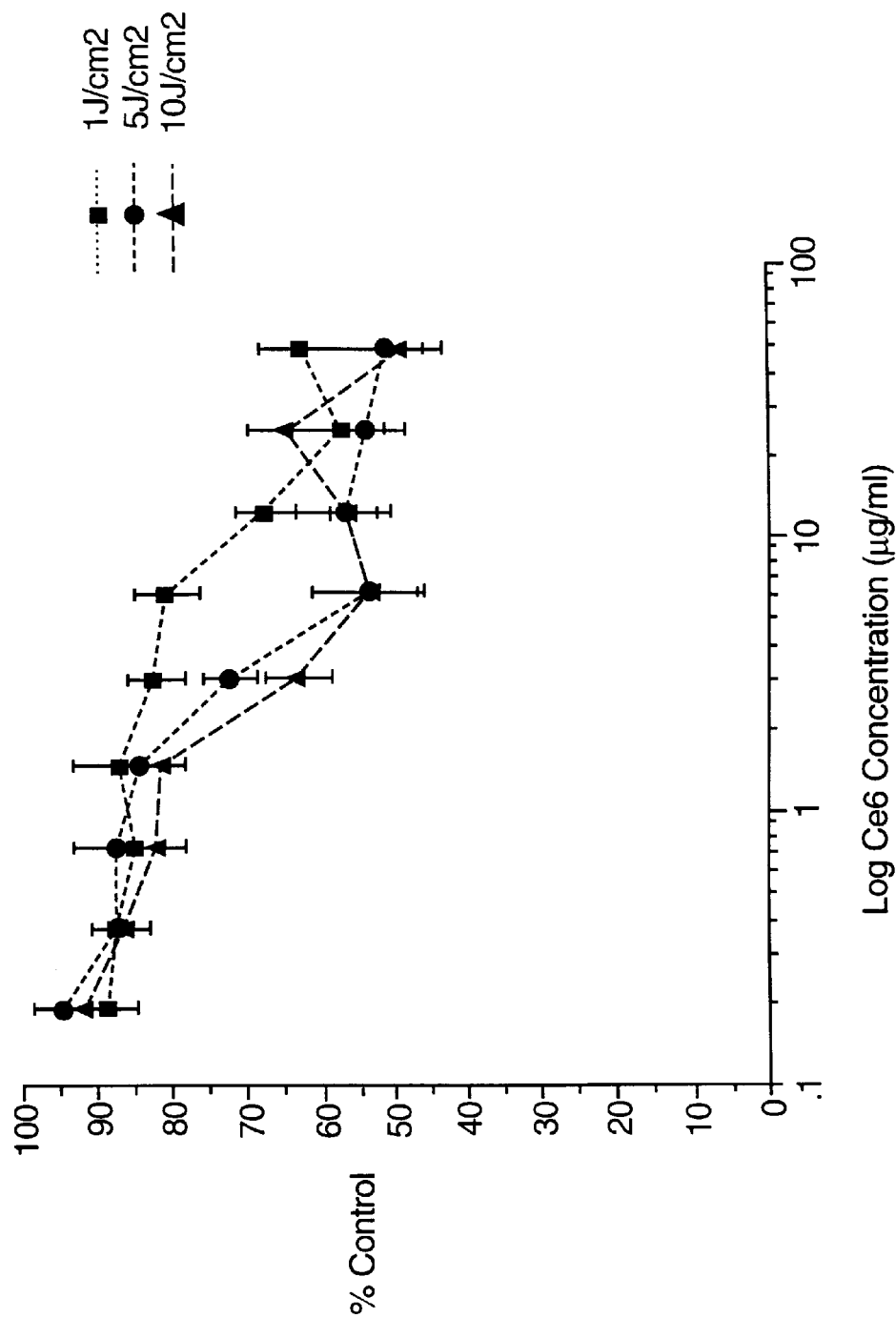
Figure 1C:
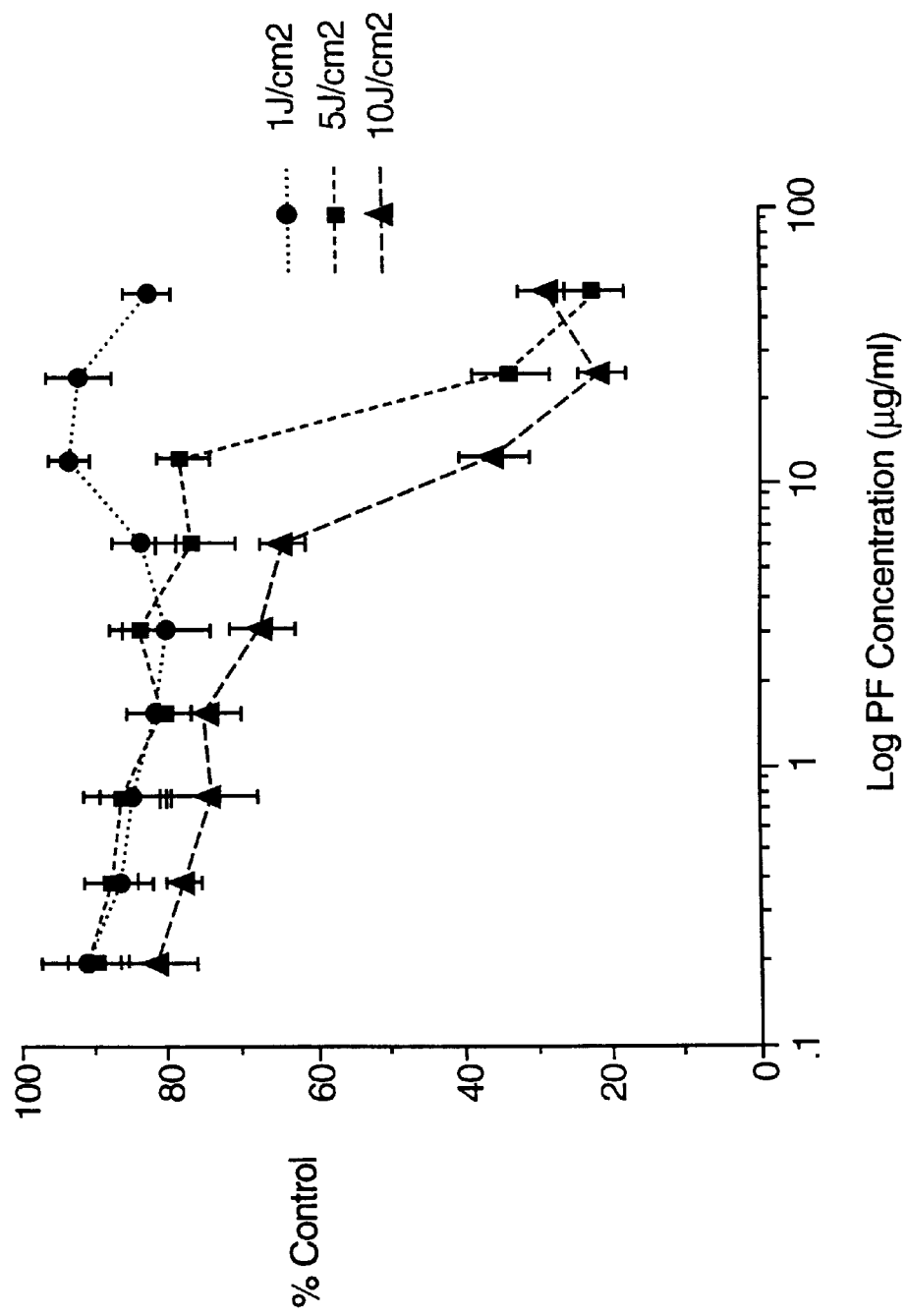

Photoactivatable chemicals localize selectively to the synovium or joint fluid and can be used to treat osteoarthritic disease. The anti-inflammatory effects of PDT and its ability to modulate enzymatic activity in chondrocytes can diminish the pathology seen in osteoarthritis. Decreased production, release, or activation of, for example, metalloproteinase enzymes, may allow for prolonged preservation of articular surfaces in oteoarthritis. Photofrin® is one of many examples of a photoactivatable therapeutic agent which may be used in the method of the invention. Its relevant characteristics, which include localization to the synovial tissue and particular clearance characteristics, are typical of many other photoactivatable compounds.

Osteoarthritis is a disease characterized by mechanically or biologically induced breakdown of articular cartilage. The degeneration of the cartilage due to biologic or mechanical effects changes load transmission through the joints and produces painful symptoms. Pain may also be due to inflammation of the joint lining tissue (synovium) which reacts to the free floating particles of cartilage (meniscal or articular). The degenerative cartilage does two things: (a) it produces enzymes which digest the extracellular matrix; and (b) it produces inflammatory mediators which spread throughout the joint and lead to inflammation of the synovium. The synovial inflammation in osteoarthritis is a response to irritating cartilage particles and is not due to an autoimmune response. PDT of osteoarthritis may slow the production of degradative enzymes, destroy inflammatory mediators in joint fluid and modulate inflammation in synovial tissue.

Numerous possibilities exist for delivery of both photosensitizing agents and light energy to the joints. Determining the most appropriate parameters for any photodynamic compound to be used for the treatment of osteoarthritis can be done using the experimental techniques provided herein.

I. Delivery of Photoactivatable Compounds

Therapeutic photoactivatable compounds may be either injected into the joints, or administered systemically according to the methods of the invention. The choice of localized versus systemic administration is determined, in part, by the number of joints to be treated during a given therapeutic regime. If a small number of joints require treatment, the therapeutic compounds may be administered locally. Conversely, if many joints require treatment, the therapeutic compounds may be administered systemically.

The therapeutic compounds to be administered for use in photodynamic therapy can be formulated for pharmaceutical or veterinary use by combination with an acceptable diluent, carrier, or excipient and/or in unit dosage form. In using therapeutic compounds in the methods of the invention, conventional pharmaceutical or veterinary practice may be employed to provide suitable formulations or compositions.

Thus, the formulations of the invention can be administered parenterally by, for example, intravenous, intraarticular, subcutaneous, intramuscular, intraventricular, intracapsular, intraspinal, intraperitoneal, topical, intranasal, or intrapulmonary administration. Patients may also be treated by oral, buccal, rectal, or vaginal administration.

Parenteral formulations may be in the form of liquid solutions or suspensions; oral formulations may be in the form of tablets, liquids, powders or capsules; and intranasal formulations may be in the form of powders, nasal drops, or aerosols.

Methods well known in the art for making formulations can to be found in, for example, Remington's Pharmaceutical Sciences, Mack Publishing Co., Easton, Pa., latest edition. Formulations for parenteral administration may, for example, contain as excipients sterile water or saline, polyalkylene glycols such as polyethylene glycol, oils of vegetable origin, or hydrogenated naphthalenes. Biocompatible, biodegradable lactide polymers or polyoxyethylene-polyoxypropylene copolymers in the form of microspheres may be used to control the in vivo release of the present compounds. Other potentially useful parenteral delivery systems for the compounds include ethylene-vinyl acetate copolymer particles, osmotic pumps, implantable infusion systems, liposomes, and antibody conjugates including, for example, liposomes into which joint tissue-specific antibodies have been incorporated. Formulations for inhalation may contain an excipient, for example, lactose; or may be aqueous solutions containing, for example, polyoxyethylene-9-lauryl ether, glycocholate and/or deoxycholate; or may be oily solutions for administration in the form of nasal drops; or a gel to be applied intranasally. Formulations for parenteral administration may also include glycocholate for buccal administration, methoxysalicylate for rectal administration, or citric acid for vaginal administration.

The present factors can be used as the sole active agents or can be used in combination with other active ingredients.

The concentration of the present factors in the formulations of the invention will vary depending upon a number of issues, including the dosage to be administered, and the route of administration.

In general terms, the compounds of the invention may be provided in an aqueous physiological buffer solution containing about 0.1 to 10% w/v compound for parenteral administration. General dose ranges for systemic administration are from about 0.01 mg/kg to about 20 mg/kg of body weight; a preferred dose range is from about 0.2 mg/kg to 2 mg/kg of body weight. When administered directly to the joint, the compounds may given at 0.01 to 10 mg per joint. The preferred dosage to be administered is likely to depend upon the type and extent of progression of the joint condition being addressed, the overall health of the patient, the patient's size, body surface area, age and sex, the formulation, and the route of administration.

II. Delivery of Photoactivating Light

Newer photosensitizing compounds, which do not cause systemic skin photosensitivity, allow for activation in the near infrared and longer wavelengths of the visible light spectrum. This allows for joint transillumination, which may be performed using a variety of devices involving laser or non-laser sources, i.e., lightboxes or convergent light beams. Alternatively, optical fibers may be passed either through arthroscopes, which will allow direct visual targeting and activation of the compounds, or directly through hypodermic needles which, preferably, have a small gauge. Light may also be passed via percutaneous instrumentation using optical fibers or cannulated waveguides. Activation may also be performed by open arthrotomy.

III. Method of Screening Therapeutic Agents for Use in Photodynamic Therapy for Osteoarthritis A. Models of Osteoarthritic Joints The following protocols may be used to generate a model of an osteoarthritic joint in a mammal. The mammal may be, for example but not restricted to, a rat, mouse, guinea pig, rabbit, dog, cat, or non-human primate. Mammals prepared in the manner described below can be used to screen various photoactivatable compounds for their application to the treatment of mechanically injured joints.

i. Section of the Medial Collateral and Both Cruciate Ligaments Combined with Resection of the Medial Meniscus The following procedure is performed with New Zealand white rabbits, but other species of rabbits and any mammals with analogous joint structures may also be used.

Adult New Zealand white rabbits ranging in weight from three to six kilograms and judged to be mature by roentgenographic demonstration of epiphyseal closure may be used. Each animal is anesthetized (for example with diabutal supplemented with Xylocaine™), and the right knee joint is entered through a median parapatellar incision. The medial collateral ligament, both cruciate ligaments, and the flexor digitorum longus tendon (the muscle has an intraarticular origin in the rabbit) are divided, and the medial meniscus is excised. The capsule is then loosely approximated and the skin is closed, for example, with a continuous nylon suture (Ehrlich et al., J. Bone and Joint Surg.—American Vol. 57:392–396, 1975).

ii. Section of the Fibular Collateral and Sesamoid Ligament and Removal of the Anterior Horn of the Lateral Meniscus Osteoarthritis may also be induced, for example in adult Dutch Belted rabbits, as described by O'Byrne et al. (Agents and Actions 39:C157–159, 1993) by sectioning the fibular collateral and sesamoid ligaments and removing the anterior horn of the lateral meniscus. This procedure has been shown to result in severe focal lesions of the cartilage on opposing surfaces of the tibia and femur (O'Byrne et al., supra).

B. Gross Pathology

Upon awakening, the animals may be permitted full weightbearing activity. Severe degenerative arthritis secondary to instability will develop over the ensuing three to six months, with visible changes apparent after one month. The knee joint may exhibit gross instability characterized by tibiofemoral and patellofemoral subluxation and occasionally by dislocation. In the early months, the articular surface of the femoral condyles, particularly that of the medial condyle, may appear dulled. In later months, fibrous tissue may cover portions of the articular surface of the tibial condyles. If the animals are allowed to survive for one year, the cartilage on the femoral surface may be thinned and exhibit focal erosion. Osteophytes may be seen on both the patella and the patellar surface of the femoral condyles.

C. Histological Analysis of the Osteoarthritic Joint

Histological studies employed to examine an osteoarthritic joint are well known to skilled artisans and include routine hematoxylin and eosin staining, and staining with safranin O, fast green, and iron hematoxylin. Hydroxyproline can be quantified by the method of Woessner; hexosamine can be quantified by the method of Rondle and Morgan; and acid phosphatase can be quantified by the method of Lowry (Lowry, J. Histochem. 1:420–428, 1953; Lowry et al., J. Biol. Chem. 207:19–37, 1954). Metabolic determinations may be performed using liquid scintillation spectrometric assays of incorporated isotopes after in vitro exposure, as described by Mankin et al. (J. Bone and Joint Surg. 51:1591–1600, 1969).

D. Animal Studies of Photodynamic Compounds Using Animals with Osteoarthritic Joints In order to determine whether a particular photoactivatable compound is suitable for use in the method of the invention, New Zealand white rabbits weighing 3–4 kg each are divided into 3 groups: a control group consisting of normal, healthy animals (control group 1), a control group consisting of animals that have undergone surgical sectioning of the anterior cruciform ligament but do not receive PDT (control group 2) and an experimental group consisting of animals that have undergone this surgery and do receive PDT. Once instability of the joint is apparent, 24 animals in the experimental group will receive a systemic injection of 2 mg/kg of the compound to be tested via a 25 gauge needle into an ear vein. Additional, localized injections may also be given 48 hours later, or at any other time indicated by drug clearance studies. A comparable number of animals in control group 1 will also receive injections of the therapeutic agent. The animals will be sedated with rompen and ketamine, according to standard protocols, and given light activation treatments. Both knees of all animals in the experimental group and one knee, preferably the right knee, of animals in control group 1 will receive light activation treatments. 400 nm–690 nm wavelength light energy, or any wavelength which is activating for the chosen therapeutic, will be transmitted via a 400 micron optical fiber through a 23 gauge needle into the knee joint cavities. Alternatively, light may be applied extracorporeally. A total light energy of 100 J/cm$^2$, or that energy range deemed appropriate for a given compound, will be applied to each joint over 20 minutes with an average laser power setting of 3–5 watts, or that wattage and time which is effective for a given compound.

Six animals from the experimental group and from control group 2, and 4 animals from control group 1 will be sacrificed one-, two-, four-, and 10 weeks after the photodynamic compound was injected into the experimental group and control group 1. After the animals have been killed, samples of synovium, articular cartilage, meniscus, and tendon will be harvested and fixed in formalin. Specimens are then embedded in paraffin, sectioned, stained with hematoxylin and eosin, and then examined microscopically for signs of inflammation, scarring, and necrosis.

It will be understood that specific modifications in dosage, timing, light wavelength, and duration may be necessary for each therapeutic compound tested. These general parameters are known to those skilled in the art and are summarized, in part, in the following papers and references cited therein which are incorporated by reference in their entirety: Gomer, J. Photochem. Photobiol. 54:1093–1107, 1991; Maziere et al., J. Photochem. Photobiol. 8:351–360, 1991; Allison et al., Photochem. Photobiol. 54:709–715, 1991; Allison et al., Photochem. Photobiol. 52:501–507, 1990; Poon et al., J. Neurosurg. 76:679–686, 1992; Reddi et al., Br. J. Cancer 61:407–411, 1990; Richter et al., Br. J. Cancer 63:87–93, 1990.

This protocol allows the practitioner to document, with pathology: (1) the ability of a photoactivatable compound to affect, e.g., inflammation at the joint, and (2) the non-deleterious effects of an activated photodynamic compound on articular cartilage, meniscus, and other periarticular tissues.

In order to document (1), samples of synovium from animals terminated at various times after treatment are fixed, embedded in paraffin, stained with a histological stain, and examined microscopically. In order to document (2), the same procedure is followed with samples of articular cartilage, meniscus, tendon, and muscle. Gross observations at the time of harvest should also be noted. Knee inflammation at the time of light application will be examined clinically and recorded. A test compound that ablates or diminishes, for example, inflammation of the joint or production of proteolytic enzymes by chondrocytes, without concomitant deleterious effects on articular cartilage, meniscus and other periarticular tissues, could be a useful compound for PDT of osteoarthritis.

The following examples are meant to illustrate, not limit, the invention.

IV. EXAMPLES

Materials and Methods

Chondrocyte Isolation

Chondrocytes were harvested by established collagenase digestion techniques. Articular cartilage was aseptically dissected from the femoral condyles and patellas of calf knee joints. Condyle surface shavings were finely minced and digested overnight at 37° C. with collagenase 1 mg/ml (Type II; 355 U/mg dry weight (dw)) and hyaluronidase 0.1 mg/ml (1060 USP/NF units/mg dw) (Worthington Biochemicals, Inc., Freehold, N.J.) in Dulbecco's Modified Eagle's Medium (DMEM; Mediatech, Herndon, Va.) supplemented with 20 mM HEPES, 100 U/ml penicillin G, 100 µg/ml ascorbic acid (serum free TCM). The resulting cell suspensions were filtered through a cell sieve and washed twice with serum free TCM. The cells were resuspended in the same medium containing 5% heat inactivated fetal calf serum (BioWhittaker, Walkerville, Md.) (FCS-TCM) for seeding. Cell number was determined using a hemocytometer. Cell viability, which was determined by trypan blue exclusion, was greater than 99% for all preparations. Cells were plated at a density of $1.5 \times 10^6$ cells/ml into Falcon 96 well cell culture plates (Becton Dickinson Labware, Franklin Lakes, N.J.) for the cytotoxicity and cell proliferation experiments and into Falcon 6 well cell culture plates for the Photosensitizer uptake studies. Chondrocyte cultures were maintained at 37° C. in a 5% $CO_2$ incubator for 1 week prior to initiation of the photosensitization studies.

Photosensitization Studies

Photofrin® (PF) and Benzoporphyrin Derivative (BPD-MA) were obtained from Quadralogic Technologies (Vancouver, Canada). Chlorin e6 (Ce6) and chloroaluminum phthalocyanine (CASP) were obtained from Ciba Geigy (Basel, Switzerland) and Porphyrin Products (Logan, Utah), respectively. All photosensitizers were added to the chondrocytes in the dark 3 hours prior to light exposure. Photosensitizer stock solutions were prepared immediately prior to each experiment; serial dilutions were prepared using FCS-TCM. All irradiations were done at the appropriate excitation wavelengths for each photosensitizer (BPD-MA 690 nm; Ce6 658 nm; CASP 680 nm; PF 624 nm) using light provided by an argon ion pumped dye laser (Coherent, Palo Alto, Calif.). Following light exposure, control and irradiated cells were maintained for 72 hours prior to the assessment of cellular viability and proliferation rates. Cells were examined daily by light microscopy for morphologic changes.

Screening studies of toxicity determined the range of doses and light response for each photosensitizer. These predetermined ranges were used for all of the studies described. For CASP, no dose response was seen. Dosages greater than 50 µg/ml were considered not clinically relevant and a dose range extending to 50 µg/ml was chosen for these studies.

Cytotoxicity Assays

PDT-induced cytotoxicity was determined 72 hours after irradiation. 3-(4,5-dimethylthiazol-2yl)-2-5-diphenyltetrazolium bromide (MTT) (Sigma Chemical Co., St. Louis, Mo.) was used for the determination of cellular viability (Mosmann, J. Immunol. Methods 65:55–63, 1983). MTT is metabolized via mitochondrial dehydrogenase enzymes to a formazan dye which can be measured spectrophotometrically. Cytotoxicity is expressed as the percentage of formazan produced in cells treated with visible light of different wavelengths and intensities relative to control cells (% control). The data are expressed as the mean ±S.E.M. from triplicate experiments.

Cell Proliferation Assays

Cell proliferation was determined by [$^3$H]-thymidine incorporation for all chondrocyte cultures 72 hours after drug and/or light exposure. The cell cultures were labeled with 5 µCi/ml [$^3$H]-thymidine (35 Ci/mmol) (ICN, Irvine, Calif.) in FCS-TCM. After incubation for 20 hours, the radioactive medium was removed and the cells were rinsed three times with phosphate buffered saline (PBS) to remove unincorporated label. The cells were then lysed with buffer containing 150 mM Tris pH 8.0, 200 mM sodium chloride, 10% triton X-100 and 1% SDS. [$^3$H]-thymidine incorporation was determined by liquid scintillation methods and the data are expressed as mean % control ±S.E.M. of samples irradiated without photosensitizer addition.

Cellular Imaging: Direct Immunofluorescence (Confocal Microscopy)

Glass coverslips were coated with 20 µg/ml fibronectin (Collaborative Biomedical Research Corp., Bedford, Mass.) at 4° C. overnight. $1.5–3 \times 10^6$ chondrocytes were seeded onto the fibronectin-coated coverslips, which were maintained at 37° C. for 2 hours prior to incubation with 10 µM rhodamine for 15 minutes. The cells were fixed with 2% formalin for 5 minutes and mounted onto histological slides. Rhodamine fluorescence was examined using an epifluorescence illumination microscope under 40× and 100× magnifications (Axiophot, Zeiss, Oberkochen, Germany). Fluorescent images resulted from rhodamine excitation using a 545 nm band pass filter for excitation and a 625 nm band pass filter for emission.

Light Microscopy

The cells were examined daily by light microscopy. Morphologic changes recorded were cellular differentiation, membrane blebbing and cellular exclusion of trypan blue.

Photosensitizer Uptake Studies

Articular chondrocytes were maintained in primary culture for five days after plating. Photosensitizer stocks were serially diluted in FCS-TCM and added to triplicate wells. The cells were incubated in the dark for 3 hours. The photosensitizer-containing FCS-TCM was then removed and the cells were rinsed with 1 ml PBS. To digest the extracellular matrix, the cells were then immersed in 1 ml of a solution of 1 mg/ml collagenase and 0.1 mg/ml hyaluronidase in serum-free TCM. The resulting single cell suspensions were transferred to microfuge tubes and were centrifuged at 3.3×g for 5 minutes. The collagenase solution was removed and the cells were rinsed three times with calcium/magnesium-free PBS. Aliquots were taken for cell counting prior to cell lysis with 1 ml 0.1 N NaOH containing 1% SDS. Cell counting was performed by hemocytometer and Coulter counter. Fluorescent spectra of the cell lysates were obtained using a Spex FluoroMax spectrofluorometer (ISA Instruments, Edison, N.J.) at the appropriate excitation/emission wavelengths for each of the four photosensitizers studied. Fluorescence spectra were corrected for background fluorescence. Relative uptake values were obtained by regression analysis of standard curves of known photosensitizer concentrations. The concentration in the cultures at which each photosensitizer inhibited chondrocyte proliferation (i.e., [$^3$H]-thymidine incorporation) by 50% ($IC_{50}$) was calculated from plots of relative proliferation (expressed as a percentage of control) versus the concentration of the photosensitizer in the culture. Values of uptake at the $IC_{50}$ are shown in fg/cell. Average protein per cell was calculated from the cell counts and protein concentration determined by the Lowry protein assay.

Gelatin Zymography

Aliquots of conditioned medium were mixed with 1 ml of acetone and maintained at $-20°$ C. for 16–20 hours. The aliquots were microcentrifuged at 14,000×g for 15 minutes, the supernatant was removed and the precipitated protein was dried in a vacuum concentrator (Savant, Farmingdale, N.Y.) to remove residual acetone. Conditioned medium samples were mixed with sample buffer (0.4 M Tris pH 6.8, 5% SDS, 20% glycerol, 0.003% bromophenol blue) and applied directly, without boiling or reduction, to 10% acrylamide gels containing 1% gelatin. After removal of SDS from the gel by incubation in 2.5% Triton X-100 for 1 hour at room temperature, the gels were incubated for 16–18 hours at 37° C. in buffer containing 50 mM Tris pH 7.6, 0.2 M NaCl, 5 mM $CaCl_2$ and 0.02% Brij 35. The gels were stained for 1 hour at room temperature in 30% methanol/10% acetic acid containing 0.5% coomassie blue R-250 and destained in the same solution without dye. The gelatinolytic activity of the proteins was evidenced by clear bands against the blue background of the stained gelatin.

Example 1

Studies of PDT Efficiency Using Several Clinically Relevant Photosensitizers

Photosensitizer Effects on Chondrocyte Morphology

In the bright field and corresponding rhodamine fluorescence images of articular chondrocytes plated onto fibronectin-coated coverslips, the cells exhibited an overall polygonal to spheroid morphology and formed confluent monolayers in primary culture. Cell density was 70–80% confluence. At plating, staining of the cells with 10 $\mu$M rhodamine indicated that >99% of the cells were metabolically active. Subcellular distribution of rhodamine as bright, discrete, punctate regions of fluorescence outside of nuclei was suggestive of mitochondrial localization. Dedifferentiation occurred in 5–10% of control cells over the seven day protocol period.

Fluorescence of Photosensitizers in Chondrocytes

Cellular and subcellular fluorescence patterns as determined by confocal microscopy varied among the photosensitizers evaluated. The strongest fluorescence signals were observed with BPD-MA, which demonstrated diffuse cytoplasmic fluorescence for all drug concentrations studied. No nuclear or membrane staining was observed. Fluorescence occurred uniformly in both differentiated and dedifferentiated chondrocytes. For Ce6, cells exhibited elevated levels of cytoplasmic fluorescence comparable in intensity and distribution to BPD-MA. Cells treated with PF demonstrated a similar cytoplasmic distribution but lower levels of fluorescence than BPD-MA. Photosensitizer uptake was observed only in differentiated chondrocytes. Minimal CASP fluorescence was observed at the drug concentrations studied; fluorescence at the highest drug concentration was difficult to visualize above baseline levels of cytoplasmic autofluorescence.

Photosensitizer Effects on Cellular Viability and Proliferation

Figure 1D:
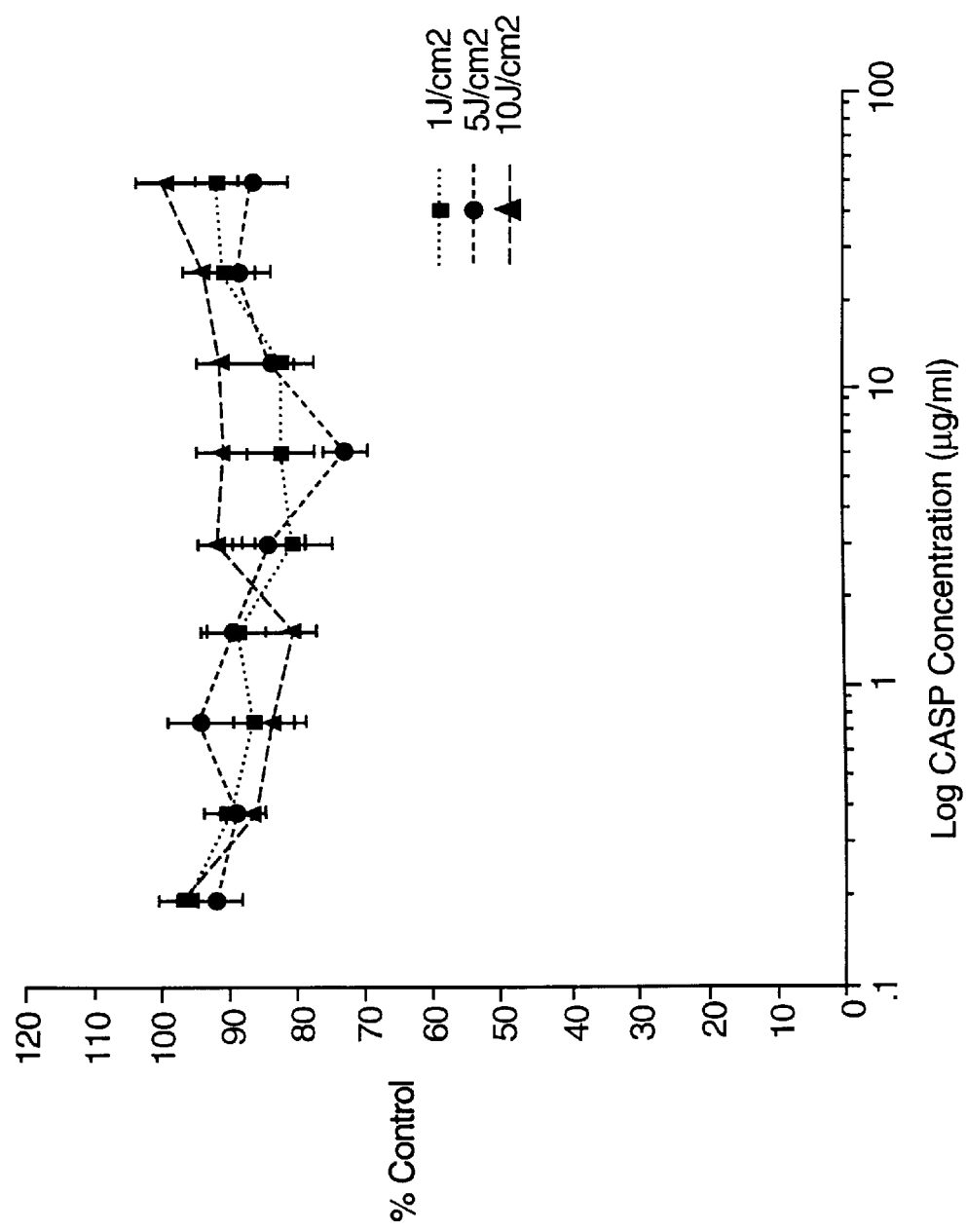

Irradiation of chondrocyte cultures with light dosages up to 10 $J/cm^2$ in the absence of photosensitizer at all wavelengths caused no decrease in cellular viability. In the presence of photosensitizer, treatment of chondrocyte cultures with 1, 5 or 10 $J/cm^2$ of light elicited general dose-dependent decreases in cellular viability (FIGS. 1A–1D). For BPD-MA (FIG. 1A) and Ce6 (FIG. 1B), saturation of toxicity effects occurred in the light dose range of 5 to 10 $J/cm^2$ and for PF (FIG. 1C) at 10 $J/cm^2$. No saturation effects were observed for CASP in the range studied (FIG. 1D). BPD-MA produced the most toxic responses in chondrocyte cultures. At BPD-MA concentrations exceeding 0.1 $\mu$g/ml, cellular viability decreased 80% for irradiations of 5 or 10 $J/cm^2$ light, and decreased by 60% for 1 $J/cm^2$ light. CASP was minimally toxic to articular chondrocytes. Irradiation of cells with 1, 5 or 10 $J/cm^2$ light in the presence of 5 $\mu$g/ml CASP attenuated cell viability by less than 20%. Cellular exposure to more than 6 $\mu$g/ml Ce6 and 5 or 10 $J/cm^2$ light decreased viability by approximately 50%. For PF concentrations greater than 12.5 $\mu$g/ml, irradiation of cell cultures with 1 $J/cm^2$ light produced less than a 10% decrease in cellular viability while irradiations at the higher fluences decreased cellular viability by nearly 70%.

Figure 2:
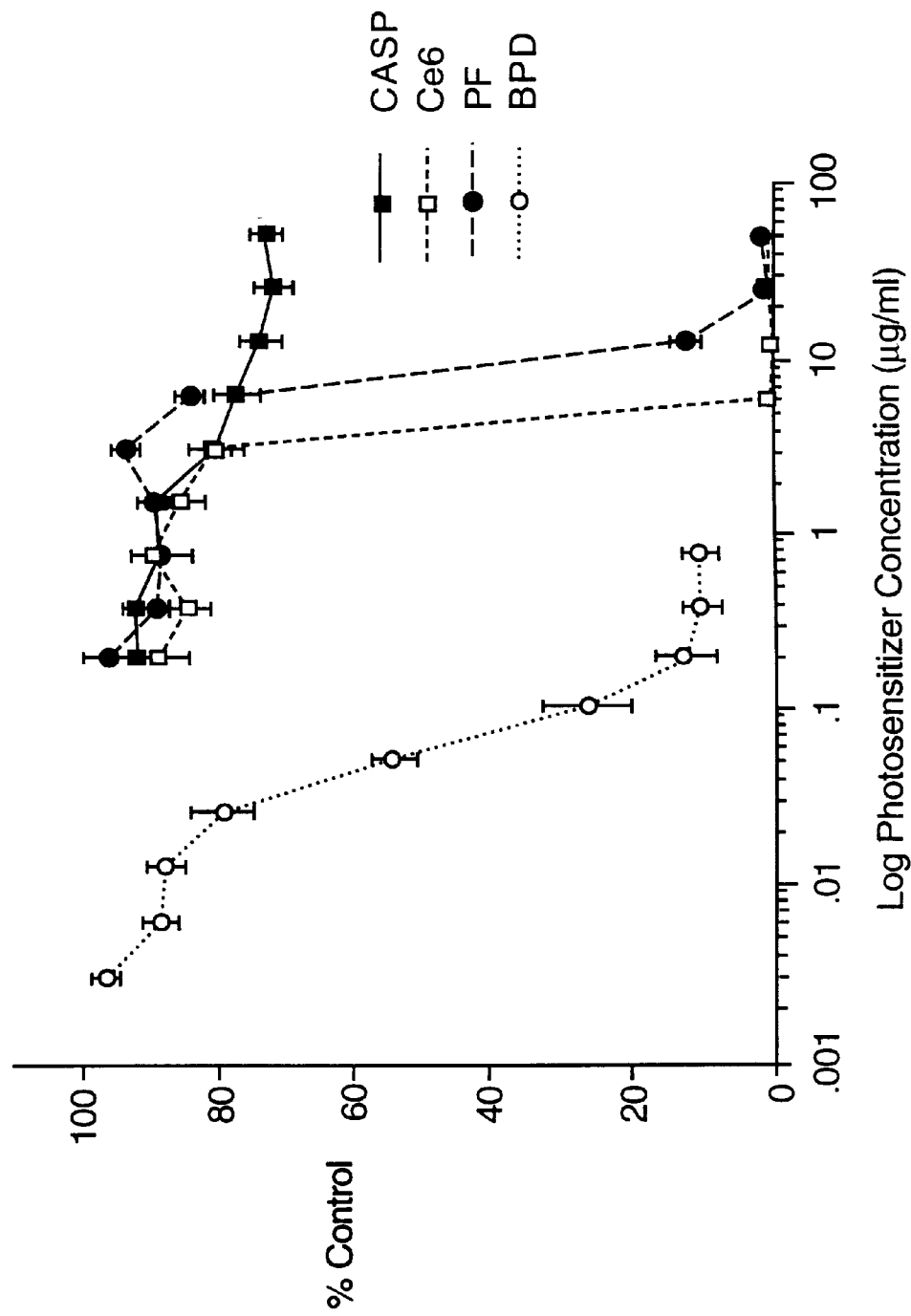
FIG. 2 is a line graph depicting the effect of PDT on chondrocyte proliferation.

All photosensitizers elicited a dose-dependent inhibitory response on cellular proliferation rates determined by [$^3$H]-thymidine incorporation (FIG. 2). BPD-MA produced the most toxic effects ($IC_{50}$=50.3 ng/ml) relative to Ce6 ($IC_{50}$=4.4 $\mu$g/ml) and PF ($IC_{50}$=9.3 $\mu$g/ml). CASP was found to be the least toxic. At the highest concentration of CASP investigated, 50 $\mu$g/ml, [$^3$H]-thymidine incorporation was reduced only 25%. The photosensitizing potentials determined by [$^3$H]-thymidine incorporation correlated with the MTT assay results.

Photosensitizer Uptake Studies

Photosensitizer uptake increased linearly across the dose range studied for all photosensitizers following a three hour incubation period. At the $IC_{50}$ concentrations, BPD-MA exhibited the lowest relative uptake. Higher uptake was observed for Ce6 which was markedly less than for CASP and PF (Table 2).

TABLE 2

In Vitro Uptake of Photosensitizers by Chondrocytes.

| Drug | $IC_{50}$ ($\mu$g/ml) | $IC_{50}$ Uptake (fg/cell) | Photons Absorbed at $IC_{50}$ (photons/cell) |
|---|---|---|---|
| BPD-MA | 0.05 | 1.02 | $5.86 \times 10^6$ |
| CASP | >50 | 64.77 | $1.86 \times 10^6$ |
| Ce6 | 4.4 | 2.32 | $1.44 \times 10^8$ |
| PF | 9.3 | 57.61 | $9.13 \times 10^6$ |

Zymography Studies

PDT effects on modulation of metalloproteinase (MMP2 and MMP9) activity, as determined by zymography, varied with the photosensitizer used, light dose applied and drug concentration. For BPD-MA and PF, MMP2 production decreased as a function of cell killing. At the $IC_{50}$ doses, MMP2 production was reduced by approximately 50% and at a highly toxic dose, production was non-detectable.

For Ce6, MMP2 production and MMP9 production were reduced at PDT parameter levels non-toxic to chondrocytes. At high drug doses, correspondingly greater decreases in MMP production occured. At the $IC_{50}$ dose, MMP2 production decreased by >95%. Total protein concentration did not vary with MMP values.

For the CASP parameters tested, no decrease in cellular viability was observed by MTT production and [$^3$H]-thymidine incorporation. However, significant reductions in MMP2 levels were recorded by zymography. At drug concentrations greater than 0.2 $\mu$g/ml and a light dose of 10 $J/cm^2$, MMP2 levels decreased by 25%. At a drug concentration of 3.12 $\mu$g/ml with a light dose of 10 $J/cm^2$ (conditions under which no decrease in cell viability was observed), complete reduction in MMP2 levels was observed.

In summary, the findings of decreased MMP production and [$^3$H]-thymidine incorporation after photodynamic treatment of the cells indicate the potential to photochemically modulate the disease process in osteoarthritis. In addition to anti-inflammatory effects on inflamed synovium, photochemical treatments may be used to retard the biologic progression of the disease, as mediated by, for example, metalloproteinase enzymes. The method described in this Example can be applied to testing a wide variety of photoactivatable compounds, such as those shown in Table 1, for utility in treatment of osteoarthritis.

Although the invention has been described with reference to the presently preferred embodiment, it should be understood that various modifications can be made without departing from the spirit of the invention. Accordingly, the invention is limited only by the following claims.

What is claimed is:

1. A method of treating a patient who has osteoarthritic disease, said method comprising
   (a) administering to the patient a therapeutic composition comprising a photoactivatable compound, or a precursor thereof; and
   (b) administering light of a photoactivating wavelength which activates the photoactivatable compound,
   wherein the amount of the therapeutic composition and the amount of light administered are sufficient to reduce the level of osteoarthritic disease in the patient.

2. The method of claim 1, wherein the photoactivatable compound is a hematoporphyrin derivative.

3. The method of claim 1, wherein the photoactivatable compound is a benzoporphyrin derivative.

4. The method of claim 1, wherein the photoactivatable compound is a product of aminolevulinic acid (ALA).

5. The method of claim 1, wherein the therapeutic composition is delivered systemically.

6. The method of claim 1, wherein the therapeutic composition is delivered locally to the area of the joint.

7. The method of claim 1, wherein the light is administered directly to the joint.

8. The method of claim 7, wherein the light is adiministered using an arthroscopic instrument.

9. The method of claim 7, wherein the light is administered using a fiber optic instrument.

10. The method of claim 1, wherein the light is administered external to the joint, transilluminating the periarticular structure of the joint.

11. The method of claim 1, wherein the light is provided by a laser light source.

12. The method of claim 1, wherein the light is provided by a non-laser light source.

13. The method of claim 1, wherein the light is derived from a broad band light source.

14. The method of claim 1, wherein the patient is a human.

15. The method of claim 1, wherein said patient is selected from the group consisting of a cat, a dog, a rabbit, a horse, a cow, a sheep, and a goat.

* * * * *

UNITED STATES PATENT AND TRADEMARK OFFICE
CERTIFICATE OF CORRECTION

PATENT NO.     : 5,942,534
DATED          : August 24, 1999
INVENTOR(S)    : Kenneth Trauner and Tayyaba Hasan It is certified that error appears in the above-identified patent and that said Letters Patent is hereby corrected as shown below:

<u>Column 1,</u>
Line 9, after "Energy" insert -- and under Grant No. N00014-94-1-0927 awarded by the Department of the Navy --

Signed and Sealed this

Third Day of September, 2002

Attest:

Attesting Officer

JAMES E. ROGAN
*Director of the United States Patent and Trademark Office*